(12) United States Patent
Qiu et al.

(10) Patent No.: US 6,809,191 B2
(45) Date of Patent: Oct. 26, 2004

(54) GM-CSF NUCLEIC ACID SEQUENCES

(75) Inventors: Jian-Tai Qiu, Rockville, MD (US);
Wan-Ching Lai, Rockville, MD (US);
Yong Liang Chu, Rockville, MD (US);
Frank Q. Li, Montgomery Village, MD (US)

(73) Assignee: Vaxim, Inc., Rockville, MD (US)

( * ) Notice: Subject to any disclaimer, the term of this patent is extended or adjusted under 35 U.S.C. 154(b) by 139 days.

(21) Appl. No.: 10/188,056

(22) Filed: Jul. 3, 2002

(65) Prior Publication Data

US 2004/0009934 A1 Jan. 15, 2004

(51) Int. Cl.$^7$ .......................... C12N 15/27; A61K 48/00
(52) U.S. Cl. .......................... 536/23.5; 514/44
(58) Field of Search ............................. 536/23.1, 23.5; 435/69.1, 69.5, 71.1, 71.2, 471, 325, 252.3, 254.11, 320.1; 530/351

(56) References Cited

U.S. PATENT DOCUMENTS

| | | |
|---|---|---|
| 5,108,910 A | 4/1992 | Curtis et al. |
| 5,298,603 A | 3/1994 | Habermann et al. |
| 5,679,356 A | 10/1997 | Bonnem et al. |
| 5,910,488 A | 6/1999 | Nabel et al. |

OTHER PUBLICATIONS

Wong et al. (1985) Science vol. 228, pp. 810–815.*
Massaer et al. (2001) Int. Arch. Allergy Immunol. vol. 125, pp. 32–43.*
Warren, et al., "Uses of Granulocyte–Macrophage Colony––Stimulating Factor in Vaccine Development", Current Opinion in Hematology, 7, 168–173 (2000).
Gribben, et al., "Development of Antibodies to Unprotected Glycosylation Sites on Recombinant Human GM–CSF", The Lancet, 335, 434–437 (1990).
Nakamura, et al., "Codon Usage Tabulated from International DNA Sequence Databases: Status for the Year 2000", Nucleic Acids Research, 28, 1, 292 (2000).
Connell, "Expression Systems for Use in Actinomycetes and Related Organisms", Current Opinion in Biotechnology, 12, 5, 446–449 (2001).
Hamm, et al., "Dose–Ranging Study of Recombinant Human Granulocyte–Macrophage Colony–Stimulating Factor in Small–Cell Lung Carcinoma", Journal of Clinical Oncology, 12, 12, 2667–2676 (1994).
Bergmann, et al., "Recombinant Human Granulocyte–Macrophage Colony–Stimulating Factor After Combined Chemotherapy in High–Grade Non–Hodgkin's Lymphoma—a Randomised Pilot Study", European Journal of Cancer, 31A, 13/14, 2164–2168 (1995).
Haas, et al., "Condon Usage Limitation in the Expression of HIV–1 Envelope Glycoprotein", Current Biology, 6, 3, 315–324 (1996).
Kotsopoulou, et al., "A Rev–Independent Human Immunodeficiency Virus Type 1 (HIV–1)–Based Vector That Exploits a Condon–Optimized HIV–1 *gag–pol* Gene", Journal of Virology, 4839–4852 (2000).

* cited by examiner

*Primary Examiner*—Prema Mertz
(74) *Attorney, Agent, or Firm*—Steven B. Kelber; Piper Rudnick LLP

(57) ABSTRACT

The present invention relates to improved methods for the treatment or prevention of disease with gene therapy or vaccines comprising host optimized GM-CSF nucleic acid sequences. More particularly, the invention provides methods for codon optimized GM-CSF with enhanced expression and adjuvant activity ex vivo and in vivo. The present invention also provides for methods of optimizing homologous gene expression ex vivo and in vitro or in transgenic animals.

15 Claims, 6 Drawing Sheets

FIGURE 1

DNA alignment Between Original (mGMCSF) and optimized sequence(m-cGM)
GenBank Access number: X02333

```
                M  A  H  E  R  K  A  K  V  L  R  R  M  W  L  Q  N  L  L  F
m-cGM:      1   atggctcacgagcggaaggctaagctgctgcgcagaatgtggctgcagaacctgctgttc   60
                ||||| |||||| | |||||||||||| ||| | || ||||||||||||||| | || |||
mGMCSF:   138   atggcccacgagagaaaagctaaggtcctgagyaggatgtggctgcagaatttactttttc   197

L  G  I  V  V  Y  S  L  S  A  P  T  R  S  P  I  T  V  T  R
m-cGM:     61   ctgggcatcgtggtgtacagcctgagcgcccccaccagaagccccatcaccgtgaccaga   120
                |||||||| ||||| ||||||||||   || ||||||| |  |||||||| || ||| |
mGMCSF:   198   ctgggcattgtggtctacagcctctcagcacccacccgctcaccatcactgtcacccgg   257

P  W  K  H  V  E  A  I  K  E  A  L  N  L  L  D  D  M  P  V
m-cGM:    121   ccctggaagcacgtggaggccatcaaggaagctctgaacctgctggacgacatgcccgtg   180
                || |||||||| || ||||||||||| |||||||||||| |||||||| |||||| ||
mGMCSF:   258   ccttggaagcatgtagaggccatcaaagaagccctgaacctcctggatgacatgcctgtc   317

T  L  N  E  E  V  E  V  V  S  N  E  F  S  F  K  K  L  T  C
m-cGM:    181   accctgaacgaggaggtggaggtggtgagcaacgagtttagctttaagaagctgacctgc   240
                ||  |||| ||  ||||| || || ||         ||||||||| ||| |||||||| || ||
mGMCSF:   318   acattgaatgaagaggtagaagtcgtctctaacgagttctccttcaagaagctaacatgt   377

V  Q  T  R  L  K  I  F  E  Q  G  L  R  G  N  F  T  K  L  K
m-cGM:    241   gtgcagacccggctgaagatcttcgagcagggactgcgggggcaactttaccaagctgaag   300
                ||||||| |||| ||||||||| |||||||| ||  ||  ||||||||| || |||||| || |||
mGMCSF:   378   gtgcagacccgcctgaagatattcgagcagggtctacggggcaatttcaccaaactcaag   437

G  A  L  N  M  T  A  S  Y  Y  Q  T  Y  C  P  P  T  P  E  T
m-cGM:    301   ggagccctgaacatgaccgccagctactaccagacctactgccctcccacacccgagacc   360
                || ||| ||||||||||| ||||||||||||||||||||| ||||||| || || || || ||
mGMCSF:   438   ggcgccttgaacatgacagccagctactaccagacatactgccccccaactccggaaacg   497

D  C  E  T  Q  V  T  T  Y  A  D  F  I  D  S  L  K  T  F  L
m-cGM:    361   gactgtgaaacccaggtgaccacctacgccgactttatcgacagcctgaagaccttcctg   420
                |||||||||||| || || |||||||| || || || || |||||||| || ||||| |||
mGMCSF:   498   gactgtgaaacacaagttaccacctatgcggatttcatagacagccttaaaacctttctg   557

T  D  I  P  F  E  C  K  K  P  V  Q  K  &  L  E  R
m-cGM:    421   accgacatcccccttcgagtgtaagaagcccgtgcagaagtgactcgagcgg
                || || |||||||| || || || || || || || || || || || |||
mGMCSF:   558   actgatatccccttgaatgcaaaaaaccagtccaaaaatga
```

Amino Acid alignment between mGMCSF and optimized sequence(m-cGM)

```
m-cGM     XbaI  CSRMAHERKAKVLRRMWLQNLLFLGIVVYSLSAPTRSPITVTRPWKHVEAIKEALNLLDD
                   ||||||||||||||||||||||||||||||||||||||||||||||||||||||||||
mGMCSF ori    ...MAHERKAKVLRRMWLQNLLFLGIVVYSLSAPTRSPITVTRPWKHVEAIKEALNLLDD      60 m-cGM         MPVTLNEEVEVVSNEFSFKKLTCVQTRLKIFEQGLRGNFTKLKGALNMTASYYQTYCPPT
              ||||||||||||||||||||||||||||||||||||||||||||||||||||||||||||
mGMCSF ori    MPVTLNEEVEVVSNEFSFKKLTCVQTRLKIFEQGLRGNFTKLKGALNMTASYYQTYCPPT     120 m-cGM         PETDCETQVTTYADFIDSLKTFLTDIPFECKKPVQK&LER XhoI
              |||||||||||||||||||||||||||||||||||
mGMCSF ori    PETDCETQVTTYADFIDSLKTFLTDIPFECKKPVQK...   159
```

GM-CSF NUCLEIC ACID SEQUENCES

BACKGROUND OF THE INVENTION

1. Field of the Invention

The present invention relates to improved recombinant mammalian, particularly human and murine, nucleic acid sequences for granulocyte macrophage-colony stimulating factor (GM-CSF) and their use in improving response to vaccines or gene therapy used for treating or preventing disease.

2. Background of the Invention

Granulocyte macrophage-colony stimulating factor, a soluble secreted glycoprotein, is a potent immunomodulatory cytokine known to facilitate development and prolongation of both humoral and cellular mediated immunity. Additional activities include, for example, activation and enhanced maturation of antigen presenting cells, increasing the expression of MHC class II antigens, activation of mature granulocytes, macrophages and monocytes, and proliferation and differentiation of hematopoietic progenitor cells. These and other diverse immunomodulatory activities have made GM-CSF an attractive investigational cytokine for use as a vaccine adjuvant for improving the immune response to vaccines, including those used for the treatment of cancer and HIV. The cDNA for GM-CSF is known and its expression in cultured cells described previously.

Several strategies have been investigated using GM-CSF as an adjuvant. GM-CSF is a soluble, secreted protein. Vaccine strategies have been described wherein soluble GM-CSF is expressed in vitro (e.g., in yeast, bacteria, or cultured mammalian cells; U.S. Pat. Nos. 5,298,603 and 5,679,356), purified, and administered concomitantly with an immunogen, which may be derived from pathogens (e.g., viruses or bacteria), or molecules associated with cancer, such as melanoma antigen (MAGE). This approach has several problems, including the cost associated with heterologous expression of GM-CSF, non-native glycosylation patterns, and the short half-life observed with systemically administered proteins, which are degraded rapidly or diffuse away from the site of the immunogen.

Fusion proteins which comprise GM-CSF in tandem with a second protein, such as an antigen as described in U.S. Pat. No. 5,108,910, have also been described for use as an adjuvant, however, these compositions suffer the same problems described above with respect to the systemic administration of a purified protein, such as limited half-life, in addition to difficulties arising from unpredictable changes in tertiary structure that may affect the biologic activity of GM-CSF. An alternative approach to administering GM-CSF protein is gene therapy wherein DNA encoding GM-CSF protein is administered and subsequently taken up by the receipient's cells and GM-CSF protein produced in vivo. This approach offers the advantages of locally sustained release of the cytokine and has proven successful in murine models (Warren T L et al., "Uses of granulocyte-macrophage colonly-stimulating factor in vaccine development," *Curr. Opin. in Hematology* 2000;7:168–173. In addition, recipient cells can be removed from the organism, transfected with GM-CSF DNA, and then reintroduced into the organism at the desired location. The expression levels observed from these approaches may be insufficient for providing the intended immunomodulatory adjuvant activity. Recombinant forms of human GM-CSF have been created with the goal of improving the activity or permitting large scale protein production, however, these sequences alter the amino acid sequence and have been associated with adverse immunologic responses, presumably due to formation of novel epitopes that result from recombinant genes or exposed native protein backbone which is normally blocked by glycosylation (Gribben et al., "Development of antibodies to unprotected glycosylation sites on recombinant human GM-CSF," *Lancet* 1990 Feb. 24; 335(8687):434–7). For example, sargramostim differs from the native human GM-CSF by one amino acid at position 23 and a different carbohydrate moiety. In contrast, the present invention provides for improved human and murine GM-CSF encoding nucleic acid sequences that encode the identical amino acid sequence as the native gene but with improved in vivo adjuvant activity. The GM-CSF nucleic acid sequences of the present invention alter select nucleotides within the native sequence without altering the amino acid sequence of the native protein.

It is well know that most amino acids are specified by more than one trinucleotide codon and that codon usage varies across species with G+C bias in mammals compared with A+T usage in microorganisms, yeast, and viruses. Selective codon usage has been further characterized by the differences in gene expression observed across different genes from the same species. Genes that are expressed with high frequency include a bias toward particular codons. The codons associated with highly expressed genes also vary with species. The different frequency of codons observed across and within species has been described and categorized by frequency of appearance in the genome (e.g., Nakamura Y., et al., "Codon usage tabulated from the international DNA sequences databases: status for the year 2000*, "Nucl. Acids Res*. 28, 292 (2000)). These differences, such as A and T preferences in the third position of a codon observed in bacteria, have been incorporated into human genes, for example, for enhancing expression of heterologous genes in microorganisms (N. D. Connell, "Expression systems for use in actinomycetes and related organisms," *Curr. Opin. Biotechnol*., 2001, October:12(5):446–9). U.S. Pat. No. 6,288,303 discusses optimizing the codon usage of mammalian genes for optimal expression in plant cells.

As described in detail herein below, the present invention provides for human and murine GM-CSF nucleic acid sequences that comprise codons associated with high expression levels in humans and mice, respectively, and surprisingly result in improved adjuvant activity compared with the native sequence.

SUMMARY OF THE INVENTION

The codon optimized mammalian, particularly human and murine GM-CSF nucleic acid sequences of the present invention, although encoding the same amino acid sequence as the native human or murine GM-CSF, provide enhanced adjuvant activity when expressed in vivo compared to the native GM-CSF gene sequence. The present invention provides modified GM-CSF DNA sequences wherein codons in the native gene have been replaced with trinucleotide codons identified in highly expressed genes of the same host (i.e., humans or mice).

The codon optimized GM-CSF sequences of the present invention preserve the native amino acid sequence encoded by the host, and therefore, all native glycosylation sites and processing signals, but result in improved biologic responses when used as a vaccine adjuvant compared to the native gene or recombinant GM-CSF genes of the prior art. The codon optimized GM-CSF nucleic acid sequences are utilized, according to the present invention, for improved biologic responses in support of prevention and treatment of disease by vaccines and gene therapy, and for research purposes.

BRIEF DESCRIPTION OF THE FIGURES

FIG. 1—Alignment of the native murine GM-CSF cDNA sequence with the codon optimized murine sequences of the present invention. The more preferred embodiment is shown immediately above the native sequence.

DETAILED DESCRIPTION OF THE INVENTION

Figure 2:
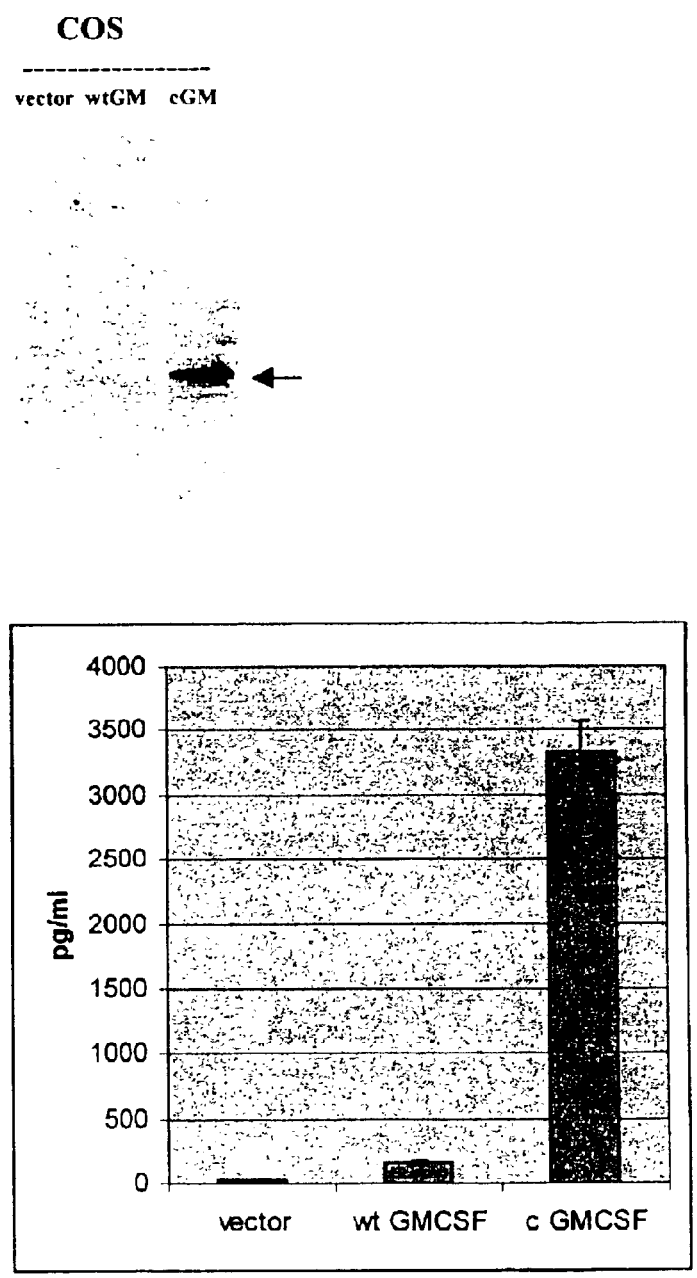
FIG. 2—Wild type ("wt") and codon optimized ("c") murine GM-CSF expression in transfected COS-7 cells. The COS-7 cells were transfected with wild type or codon optimized murine GM-CSF DNA constructs. Cell lysates from control vector pcDNA3.1-, pwt-GMCSF- and pc-GMCSF-transfected cells were separated by SDS-PAGE, transferred to nitrocellulose membranes, and analyzed by immunoblotting with a rabbit anti-murine GM-CSF antibody (top panels). Soluble GM-CSF released from transfected cells was monitored by ELISA (bottom panel).

The wild type human and murine GM-CSF cDNA sequences were optimized by first identifying codons within the cDNA which are not associated with the codon usage in highly expressed genes in humans and mice, respectively. Each sub-optimal codon is replaced with those identified from highly expressed genes of the same species, which are known in the art and available online, for example, at http://www.kazusa.or.jp/codon/. This usually requires only by a single base change in the third position but may also require changes in the second position. The codon optimized sequences can be prepared entirely by cDNA synthesis or created from wild type cDNA using molecular cloning methods well known in the art (e.g., Maniatis, T. 1989. "Molecular Cloning: A Laboratory Manual," Cold Spring Harbor Laboratory Press, NY, vol 1, 2, 3).

This invention embraces the optimized gene sequences encoding mammalian GM-CSF together with their use as an adjuvant in gene therapy or in connection with vaccines to obtain a stronger immunoresponse to expressed proteins. The methods, per se, do not constitute part of the invention, save for the use of the novel optimized sequences addressed herein. Representative formulations, dosages and administration, such as those established for human patients, can be found with respect to GM-CSF in Hamm et al, *J. Clin. Oncol.* December 1994; 12(12):2667–76 and Bergmann et al., *Eur. J. Cancer* December 1995; 31A(13–14): 2164. The utilization of the inventive subject matter is in manner not distinguishable per se from conventional DNA delivery techniques in connection with gene therapy and vaccines. Both ex vivo and in vivo utilities are embraced by the invention.

In particular, the sequences of this invention can be used in conjunction with a wide variety of DNA vaccines, where the effective composition includes as effective elements DNA, either naked or in the form of modified vectors, together with an appropriate carrier and the codon optimized GM-CSF DNA of the invention. Appropriate carriers include everything from saline solutions for conventional IM preparations to gene guns and preparations therefor to liposome complexes.

The inventive sequences of this invention are also suitable for use in ex vivo and in vivo cancer therapies, including radiation and chemotherapeutic treatment of cancer cells, particularly tumor cells, which have been transduced/transfected with GM-CSF vectors, commonly in the form of adenoviral vectors carrying GM-CSF as a heterologous transgene. Other transfer means are set forth, e.g., in U.S. Pat. No. 5,910,488.

Those of skill in the art will appreciate that there is a large, but finite number of combinations of codon bases that can be utilized to optimize expression. The invention embraces any optimization of mammalian, particularly human and murine, GM-CSF sequences. Among prefexred embodiments is that set forth in FIG. 1.

EXAMPLE

This invention is further illustrated by reference to the example set forth below. In the example, the murine GM-CSF sequence has been codon optimized. The same methods can be used to optimize other mammalian sequences encoding GM-CSF, including, preferably, human with predictably similar results. The degree of enhanced activity will depend, in part, on the completeness of optimization. Optimization of a single codon may have limited impact, in contrast with the optimization of a plurality of codons of a given sequence. All the alternatives are embraced within the invention exemplified herein.

Experimental Protocol and Results

Construction of murine GM-CSF expression vectors. The native sequences coding for the 153 amino acids (aa) of murine GM-CSF (GenBank accession no. X02333; FIG. 1 upper sequence) was amplified by PCR and cloned into pcDNA3.1(-) downstream from the human CMV immediate-early promoter (Pcmv) sequence, using BamH I sites to generate pm-wtGMCSF. To generate pm-cGMCSF, the codon modified form of murine GMCSF, we changed the codon usage to that utilized by highly expressed human genes as described recently for HIV-1 gp120 and gag-pol (Haas, J., E. Park, and B. Seed. 1996. Codon usage limitation in the expression of HIV-1 envelope glycoprotein. Curr. Biol. 6:315–32; Kotsopoulou E, Kim V N, Kingsman A J, ingsman S M, and Mitrophanous K A. 2000. A Rev-independent human immunodeficiency virus type 1 (HIV-1)-based vector that exploits a codon-optimized HIV-1 gag-pol gene. J Virol 74(10):4839–52).

The resulting modified murine GM-CSF encoding a protein without any amino acid change (FIG. 1 lower sequence). The resulting 480-bp gene cassette included the XbaI and Xho I cloning sites and was constructed synthetically by the Aptagen Company (Herndon, Va.). This modified murine GM-CSF sequence was cloned into the XbaI and Xho I restriction sites of the eukaryotic expression vector pcDNA3.1(−) that employs the cytomegalovirus (CMV) immediate-early enhancer/promoter and bGH terminator (Invitrogen, San Diego, Calif.), resulting in the plasmid pm-cGMCSF. The CMV promoter provides a high level of constitutive expression in a range of mammalian cells. The BGHpA signal provides efficient transcription termination and polyadenylation of mRNA.

Comparison of murine GM-CSF expression by the various constructs in primate cells. We initially tested the protein expression by various murine GM-CSF expression vectors in transfected COS-7 cells, an African green monkey kidney-derived cell line. When cell lysates from transfected COS-7 cells were analyzed by immunoblotting with a rabbit anti-murine GM-CSF antibody, GM-CSF precursor protein was not detected in pcDNA3.1-transfected COS-7 cells, as expected (FIG. 2, lane 1, top panel). Also, GM-CSF protein was not detected in pm-wtGMCSF-transfected COS-7 cells (FIG. 2, lane 2, top panel). GM-CSF protein was detected in transfected COS-7 cells with the pm-cGMCSF constructs (FIG. 2, top panel).

The secreted GM-CSF protein was also detected in culture supernatants of pm-cGMCSF-transfected COS-7 cells by the rabbit anti-murine GM-CSF antibody (FIG. 2, bottom panel). As expected, no GM-CSF protein was detected in culture supernatants of pcDNA3.1 (lane 1)-transfected COS-7 cells (FIG. 2, bottom panel). Again, the pm-cGMCSF-transfected COS-7 cells produced much more GM-CSF proteins than the pm-wtGMCSF-transfected COS-7 cells (FIG. 2, bottom panel). These results suggest that the mutations modifying the codon usages in the murine GM-CSF coding sequence increase GM-CSF expression in COS-7 cells.

Figure 3:
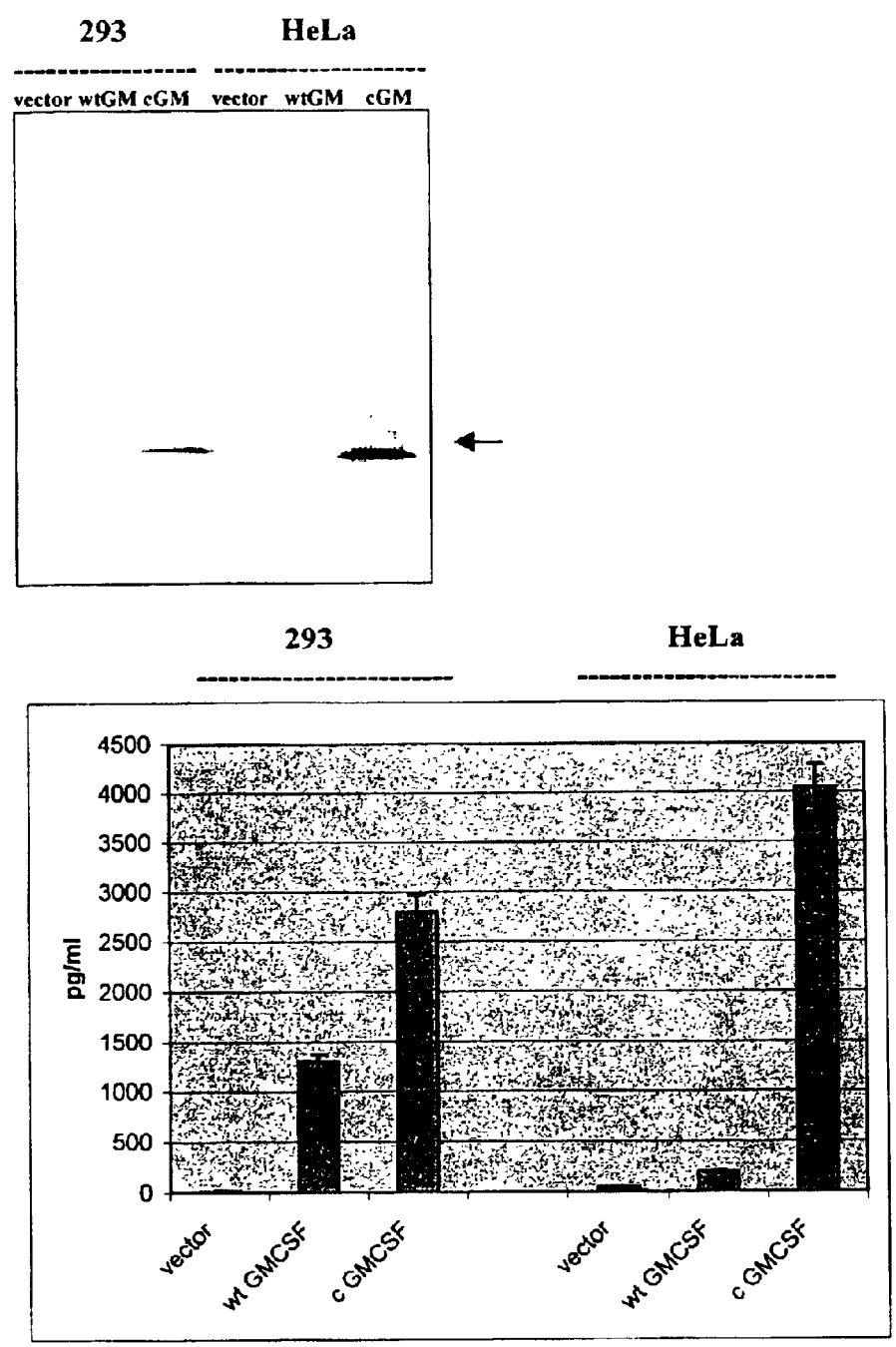
FIG. 3—Murine GM-CSF expression in transfected 293 and HeLa cells. The 293 and HeLa cells were transfected with wild type or codon optimized murine GM-CSF DNA constructs. Cell lysates from control vector pcDNA3.1-, pwt-GMCSF- and pc-GMCSF-transfected cells were separated by SDS-PAGE, transferred to nitrocellulose membranes, and analyzed by immunoblotting with a rabbit anti-murine GM-CSF antibody (top panels). Soluble GM-CSF released from transfected cells was monitored by ELISA (bottom panel).

Comparison of HIV-1 Gag expression by the various constructs in human cells. GM-CSF expression was also evaluated with the various constructs in transfected 293 cells, a human embryonal kidney epithelial cell line and HeLa cells. Immunoblot analysis of cell lysates prepared from transfected 293 cells is shown in FIG. 3 (top panel). Transfection of the 293 cells with pcDNA3.1 or pm-wtGMCSF did not produce detectable levels of GM-CSF protein by immunoblot analysis (FIG. 3, top panel, lanes 1 and 2). On the other hand, pm-cGMCSF-transfected 293 cells produced detectable GM-CSF (FIG. 3). GM-CSF protein was also detected in the supematants of pm-cGMCSF and pm-wtGMCSF-transfected 293 cells (FIG. 3, bottom panel) but no GM-CSF was detected in the supematants of pcDNA3.1-transfected 293 cells (FIG. 3, bottom panel). Again, the pm-cGMCSF-transfected 293 cells produced much more GM-CSF proteins than the pm-wtGMCSF-transfected 293 cells.

To compare levels of GM-CSF protein expression in human cancer cells by the various murine GM-CSF constructs, we performed transient transfection experiments using HeLa cells. Three days after transfection, cell lysates from transfected HeLa cells were analyzed by immunoblotting for the presence of cell-associated GM-CSF molecules (FIG. 3, top panel). GM-CSF was only detected in the cell lysates of HeLa cells transfected by pm-cGMCSF (lane 6, FIG. 3, top panel). No GM-CSF was detected in the cell lysates of pcDNA3.1- and pm-wtGMCSF-transfected HeLa cells by rabbit anti-murine GM-CSF antibody (FIG. 3, top panel, lanes 4 and 5). GM-CSF was also detected in the supernatants of pm-cGMCSF-transfected HeLa cells (FIG. 3, bottom panel). No GM-CSF was detected in the supernatants of pcDNA3.1-transfected HeLa cells (FIG. 3, bottom panel).

Figure 4:
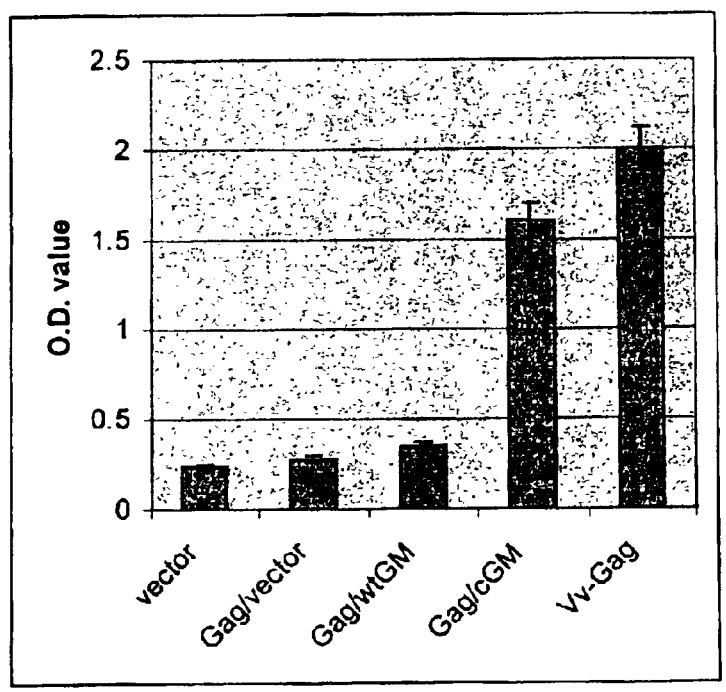
FIG. 4—Immune responses to HIV-1 GAG in BALB/c mice coinjected with pGMCSF/pcGMCSF and pGag DNA plasmids. Mice were coinjected i.m. with 50 µg pGag and a total of 50 µg pwt-GMCSF or pc-GMCSF and or with corresponding control vector plasmids respectively, as indicated. Plasmid doses were divided in half between the two gastrocnemius muscles. Anti-Gag antibodies were evaluated after vaccinia virus challenge. Serum IgG reactivity to pGag was measured by ELISA using recombinant HIV-1 Gag as coating antigen. Sera were tested as a pool of 3 sera diluted 1:300. Vaccinia/Gag, sera from mice infected with recombinant vaccinia virus/Gag as a positive control. Background OD values of preimmune serum at 1:300+2 SD (0.1) were subtracted.

Anti-Gag antibody responses in mice immunized with naked DNA vaccine. BALB/c mice were intramuscularly injected with total 100 μg of plasmid DNA two times at 0 and 2 weeks. Anti-Gag antibodies were measured after virus challenge. Sera were collected from the mice injected with the different DNA constructs and analyzed by immunoblot using purified Gag p55 recombinant protein from *Escherichia coli*. As shown in FIG. 4, anti-Gag antibodies were detected in mice vaccinated with either pGAG/wt-GM (lane 3) or pGAG/cGM DNA mixture (lane 4) and in mice infected with recombinant vaccinia virus/Gag (lane 5). In contrast, no anti-Gag antibodies were detected in mice immunized with pcDNA3.1 and pGAG/vector DNA mixture (FIG. 4, lanes 1 and 2). Administration of pGAG plasmid alone did not induced detectable IgG antibody responses. The co administration of the wild type GM-CSF plasmid induced only a modest increase in total IgG anti-Gag serum titers. By comparison, co administration of the codon modified GM-CSF plasmid significantly increased total IgG serum titers.

Figure 5:
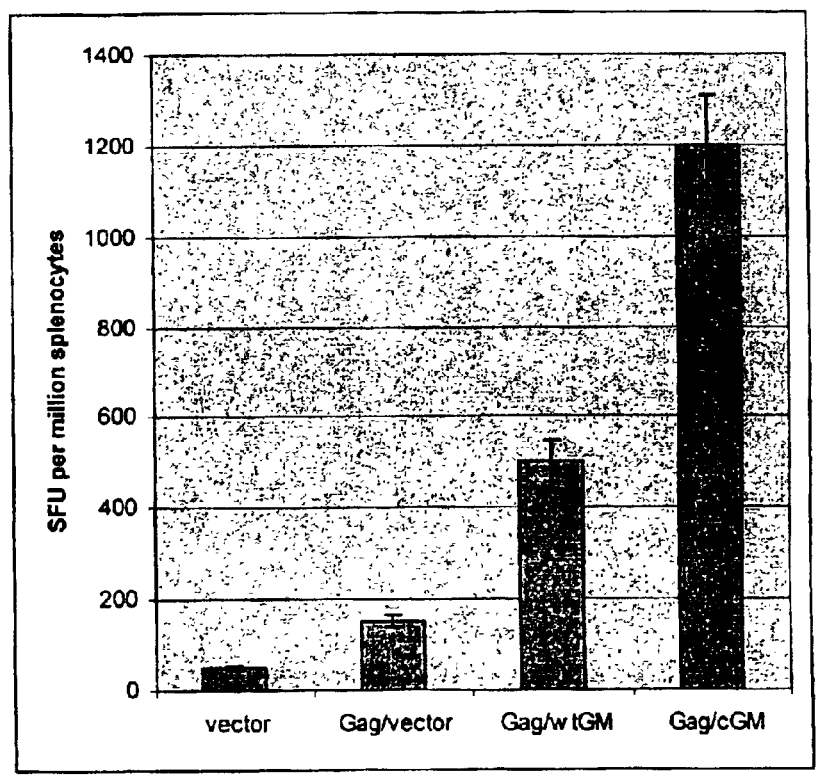
FIG. 5—ELISPOT assay. Mice were coinjected i.m. twice two weeks apart with 50 µg pGag and a total of 50 µg pwt-GMCSF or pc-GMCSF and or with corresponding control vector plasmids respectively, as indicated. Plasmid doses were divided in half between the two gastrocnemius muscles. Immunized mice were i.p. challenged with a recombinant vaccinia virus vector encoding HIV-1 Gag ($10^7$ PFU per mouse) at 35 days after the final DNA vaccination. Splenocytes were harvested 5 days after the recombinant vaccinia virus challenge. The spot numbers are the means of the triplicates. Error bars indicate the standard deviations from triplicated cultures.

ELISPOT assay in DNA-vaccinated mice. Antigen-specific CD8$^+$ T cell responses were measured by two methods: IFN-γ ELISPOT assay and Intracellular cytokine staining and flow cytometry analysis. Mice were immunized with the various DNA constructs as described above. At Day 5 after recombinant vaccinia virus challenge, splenocytes from the mice in each group were harvested and pooled, and the IFN-γ ELISPOT assay specific to HIV-1 Gag peptide were measured following antigen stimulation. As expected, those plasmids that did not express Gag p55 in vitro, such as pcDNA3.1 did not elicit an antigen-specific CD8$^+$ T cell response against HIV-1 Gag (FIG. 5). A 3-fold increase in numbers of cells secreting Ag-specific IFN-γ to either peptide was detected in mice immunized with the addition of wild type GM-CSF plasmid (500 SFU vs. 170 SFU, FIG. 5, lane 3 vs. 2). The group of vaccinated mice that received pm-cGMCSF developed a slightly higher level of HIV-1 Gag-specific CD8$^+$ activity than those that received pm-wtGMCSF. These results showed that intramuscular injection of the mixture of pGAG and codon modified GM-CSF plasmids had larger numbers of IFN-γ secreting cells that remained elevated longer after the second immunization and can induce both humoral and cellular immune responses against HIV-1 Gag in a murine model. Intracellular cytokine staining and flow cytometry analysis. CD8$^+$ T lymphocytes are one of the most crucial components of antiviral effector cells. We therefore assessed the number of HIV-1 Gag-specific CD8$^+$ T cells expressing IFN-γ in the spleens of mice immunized with DNA vector and challenged with vP1287. These cells were measured by brief stimulation in vitro for 24 h with MHC class I-restricted HIV p24 peptide (amino acid sequence: AMQMLKETI), followed by staining for CD8 and intracellular IFN-γ.

Figure 6:
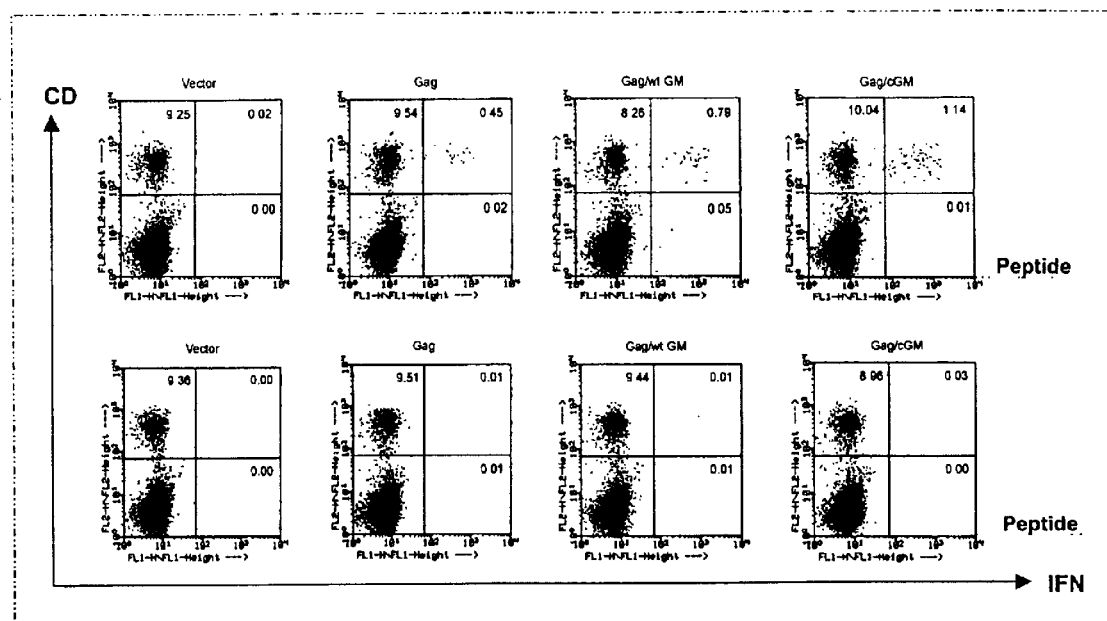
FIG. 6—Intracellular cytokine staining and flow cytometry analysis. Mice were coinjected i.m. twice two weeks apart with 50 µg pGag and a total of 50 µg pwt-GMCSF or pc-GMCSF and or with corresponding control vector plasmids respectively, as indicated. Plasmid doses were divided in half between the two gastrocnemius muscles.

Intracellular cytokine staining and ELISPOT are sensitive functional assays used to measure the IFN-γ production at the single-cell level. We observed a high level of Gag-specific CD8$^+$ effector cells in the spleens of mice co immunized with the mixture pGAG plasmid and pm-cGMCSF plasmid (1.14% of the total splenocytes and 10.2% of the total CD8+ T cells) within 5 days of vP1287 challenge (FIG. 6). In contrast, less than 0.02% of the total splenocytes were CD8+ T cells expressing IFN-γ in control vector-immunized mice. The level of Gag-specific CD8+ effector cells in the spleens of mice immunized with pm-wtGMCSF plasmid (0.79% of the total splenocytes and 8% of the total CD8+ T cells) was lower than that obtained with pm-c-GMCSF. The background level in mice immunized with pcDNA3.1 and challenged with recombinant vaccinia virus expressing HIV-1 Gag was low, suggesting that Gag-specific CD8+ IFN-γ-producing cells were generated from memory T cells.

For application of the above example to other codons and other optimization solutions, reference to the following sequences may be of value.

Sequences

Bolded trinucleotides, shown below in the native and codon optimzied sequences, are representative of those codons which may be modified according to the present invention.

```
Native Human Exon 1:
Seq. ID NO: 1:
ATGTGGCTGCAGAGCCTGCTGCTCTTGGGCACTGTGGCCTGCAGCATC

TCTGCACCCGCCCGCTCGCCCAGCCCCAGCACGCAGCCCTGGGAGCAT

GTGAATGCCATCCAGGAGGCCCGGCGTCTCCTGAACCTGAGTAGAGAC

ACT

Codon Optimized Human Exon 1:
Seq. ID NO: 2:
atgtggctgcagagcctgctcctgctgggcaccgtggcctgcagcatc agcgctcccgccagaagcccagccctccacccagccctgggagcac gtgaacgccatccaggaggccagacggctgctgaacctgtccagagac acc Seq. ID NO:3:
atgtggctgcagagcctgctgctcctgggcaccgtggcctgcagcatc agcgccccgcccgctcgcccagccccagcacgcagccctgggagcac gtgaacgccatccaggaggcccgggcgctcctgaacctgagccgcgac acc Seq. ID NO:4:
atgtggctgcagagcctgctgctcctcggcactgtggcctgcagcatc tccgcacccgcccgctcgcccagccccagcacgcagccctgggagcat gtgaatgccatccaggaggcccggcgtctcctgaacctgtccagagac act Seq. ID NO:5:
atgtggctgcagagcctgctgctcctcggcaccgtggcctgcagcatc tccgccccgcccgctcgcccagccccagcacgcagccctgggagcac gtgaacgccatccaggaggcccgggcgctcctgaacctgtcccgcgac acc Native Human Exon 2:
Seq. ID NO:6:
GCTGCTGAGATGAATGAAACAGTAGAAGTCATCTCAGAAATGTTTGACCTCCAG Codon Optimized Human Exon 2:
Seq. ID NO: 7:
gccgccgagatgaacgagaccgtggaggtgatcagcgagatgttcgacctgcag Seq. ID NO: 8:
gccgccgagatgaacgaaaccgtggaggtcatcagcgaaatgtttgacctccag Seq. ID NO: 9:
gccgccgagatgaatgagaccgtggaagtcatcagcgagatgttcgacctccag Native Human Exon 3:
Seq. ID NO: 10:
GAGCCGACCTGCCTACAGACCCGCCTGGAGCTGTACAAGCAGGGCCTG
```

-continued

CGGGGCAGCCTCACCAAGCTCAAGGGGCCCCTTGACCATGATGGCCAGC

CACTACAAGCAGCACTGCCCTCCAACCCCG

Codon Optimized Human Exon 3:
Seq. ID NO: 11:
gagcccacctgtctgcagacccggctggagctgtacaagcaggggactg cggggcagcctgaccaagctgaagggacccctgaccatgatggccagc cactacaagcagcactgccctcccacaccc

Seq. ID NO: 12:
gagccgacctgcctgcagacccgcctggagctgtacaagcagggcctg cgcggcagcctcaccaagctcaagggccccctgaccatgatggccagc cactacaagcagcactgcccccccaccccg Seq. ID NO: 13:
gagccgacctgcctccagacccgcctggagctgtacaagcagggcctg cgcggcagcctcaccaagctcaagggccccctcaccatgatggccagc cactacaagcagcactgcccccccaccccg Seq. ID NO: 14:
gagccgacctgcctgcagacccgcctggagctgtacaagcagggcctg cgcggcagcctcaccaagctcaagggccccctcaccatgatggccagc cactacaagcagcactgcccccccaccccg Native Human Exon 4 encoding Ile at position 117:
Seq. ID NO: 15:
GAAACTTCCTGTGCAACCCAGATTATCACCTTTGAAAGTTTCAAAGAG

AACCTGAAGGACTTTCTGCTTGTCATCCCCTTTGACTGCTGGGAGCCA

GTCCAGGAGTGA

Codon Optimized Human Exon 4:
Seq. ID NO: 16:
gagaccagctgcgccacccagatcatcaccttcgagagcttcaaggag aacctgaaggacttcctgctggtgatccccttcgactgctgggagccc gtgcaggagtga

Seq. ID NO: 17:
gagacctcctgcgccacccagatcatcaccttcgagagcttcaaggag aacctgaaggacttcctgctggtcatccccttcgactgctgggagccc gtccaggagtga

Seq. ID NO: 18:
gagacctcctgcgccacccagatcatcaccttcgagagcttcaaggag aacctgaaggacttcctgctcgtcatccccttcgactgctgggagccc gtccaggagtga

Seq. ID NO: 19:
gagacctcctgcgccacccagatcatcaccttcgagtccttcaaggag aacctgaaggacttcctgctggtcatccccttcgactgctgggagccc gtccaggagtga

Seq. ID NO: 20:
gaaacctcctgtgccacccagatcatcaccttcgaaagcttcaaggag aacctgaaggacttcctgctggtcatccccttcgactgctgggagccc gtccaggagtga

Seq. ID NO: 21:
gagacctcctgcgccacccagatcatcaccttcgagtccttcaaggag

-continued
```
aacctgaaggacttcctgctcgtcatccccttcgactgctgggagccc gtccaggagtga
```

Native Human Exon 4 encoding Thr at position 117:
SEQ. ID NO. 28:
```
GAAACTTCCTGTGCAACCCAGACTATCACCTTTGAAAGTTTCAAAGAG

AACCTGAAGGACTTTCTGCTTGTCATCCCCTTTGACTGCTGGGAGCCA

GTCCAGGAGTGA
```

Codon Optimized Human Exon 4:
Seq. ID NO: 22:
```
gagaccagctgcgccacccagaccatcaccttcgagagcttcaaggag aacctgaaggacttcctgctggtgatccccttcgactgctgggagccc gtgcaggagtga
```

Seq. ID NO: 23:
```
gagacctcctgcgccacccagaccatcaccttcgagagcttcaaggag aacctgaaggacttcctgctggtcatccccttcgactgctgggagccc gtccaggagtga
```

Seq. ID NO: 24:
```
gagacctcctgcgccacccagaccatcaccttcgagagcttcaaggag aacctgaaggacttcctgctcgtcatccccttcgactgctgggagccc gtccaggagtga
```

Seq. ID NO: 25:
```
gagacctcctgcgccacccagaccatcaccttcgagtccttcaaggag aacctgaaggacttcctgctggtcatccccttcgactgctgggagccc gtccaggagtga
```

Seq. ID NO: 26:
```
gaaacctcctgtgccacccagatcatcaccttcgaaagcttcaaggag aacctgaaggacttcctgctggtcatccccttcgactgctgggagccc gtccaggagtga
```

Seq. ID NO: 27:
```
gagacctcctgcgccacccagaccatcaccttcgagtccttcaaggag aacctgaaggacttcctgctcgtcatccccttcgactgctgggagccc gtccaggagtga
```

Codon optimized (co) (SEQ ID NO.: 29) murine GM-CSF compared
to wild type (wt) (SEQ ID NO.: 30) murine
GM-CSF (Genbank accession no. X02333)
```
co  atggctcacgagcggaaggctaaggtgctgcgcagaatgtggctgcagaacctgctgttc wt  atggcccacgagagaaaggctaaggtcctgaggaggatgtggctgcagaatttacttttc co  ctgggcatcgtggtgtacagcctgagcgcccccaccagaagcccatcaccgtgaccaga wt  ctgggcattgtggtctacagcctctcagcacccacccgctcacccatcactgtcacccgg co  ccctggaagcacgtggaggccatcaaggaagctctgaacctgctggacgacatgcccgtg wt  ccttggaagcatgtagaggccatcaaagaagccctgaacctcctggatgacatgcctgtc co  accctgaacgaggaggtggaggtggtgagcaacgagtttagctttaagaagctgacctgc wt  acattgaatgaagaggtagaagtcgtctctaacgagttctccttcaagaagctaacatgt co  gtgcagacccggctgaagatcttcgagcagggactgcggggcaactttaccaagctgaag wt  gtgcagacccgcctgaagatattcgagcagggtctacggggcaatttcaccaaactcaag co  ggagcccctgaacatgaccgccagctactaccagacctactgccctcccacacccgagacc
```

-continued

```
wt  ggcgccttgaacatgacagccagctactaccagacatactgcccccaactccggaaacg co  gactgtgaaacccaggtgaccacctacgccgactttatcgacagcctgaagaccttcctg wt  gactgtgaaacacaagttaccacctatgcggatttcatagacagccttaaaacctttctg co  accgacatccccttcgagtgtaagaagcccgtgcagaagtgactcgagcgg wt  actgatatcccctttgaatgcaaaaaaccagtccaaaaatga
```

Codon optimized (co) (SEQ ID NO.: 31) human GM-CSF compared
to wild type (wt) (SEQ ID NO.: 30) human GM-CSF
encoding Ile at position 117 (Genbank accession no. X03021)

```
co  atgtggctgcagagcctgctcctgctgggcaccgtggcctgcagcatcagcgctcccgcc wt  atgtggctgcagagcctgctgctcttgggcactgtggcctgcagcatctctgcacccgcc co  agaagcccagcccctccacccagccctgggagcacgtgaacgccatccaggaggccaga wt  cgctcgcccagccccagcacacagccctgggagcatgtgaatgccatccaggaggcccgg co  cggctgctgaacctgtccagagacaccgccgccgagatgaacgagaccgtggaggtgatc wt  cgtctcctgaacctgagtagagacactgctgctgagatgaatgaaacagtagaagtcatc co  agcgagatgttcgacctgcaggagcccacctgtctgcagacccggctggagctgtacaag wt  tcagaaatgtttgacctccaggagccgacctgcctacagacccgcctggagctgtacaag co  cagggactgcggggcagcctgaccaagctgaagggacccctgaccatgatggccagccac wt  cagggcctgcggggcagcctcaccaagctcaagggcccttgaccatgatggccagccac co  tacaagcagcactgccctcccacacccgagaccagctgcgccacccagatcatcaccttc wt  tacaaacagcactgccctccaaccccggaaacttcctgtgcaacccagattatcacctt co  gagagcttcaaggagaacctgaaggacttcctgctggtgatcccttcgactgctgggag wt  gaaagtttcaaagagaacctgaaggactttctgcttgtcatccccttttgactgctgggag co  cccgtgcaggagtga wt  ccagtccaggagtga
```

Codon optimized (co) (SEQ ID NO.: 33) human GM-CSF compared
to wild type (wt) (SEQ ID NO.: 34) human GM-CSF
encoding Thr at position 117 (Genbank accession no. M10663)

```
co  atgtggctgcagagcctgctcctgctgggcaccgtggcctgcagcatcagcgctcccgcc wt  atgtggctgcagagcctgctgctcttgggcactgtggcctgcagcatctctgcacccgcc co  agaagcccagcccctccacccagccctgggagcacgtgaacgccatccaggaggccaga wt  cgctcgcccagccccagcacacagccctgggagcatgtgaatgccatccaggaggcccgg co  cggctgctgaacctgtccagagacaccgccgccgagatgaacgagaccgtggaggtgatc wt  cgtctcctgaacctgagtagagacactgctgctgagatgaatgaaacagtagaagtcatc co  agcgagatgttcgacctgcaggagcccacctgtctgcagacccggctggagctgtacaag wt  tcagaaatgtttgacctccaggagccgacctgcctacagacccgcctggagctgtacaag co  cagggactgcggggcagcctgaccaagctgaagggacccctgaccatgatggccagccac wt  cagggcctgcggggcagcctcaccaagctcaagggcccttgaccatgatggccagccac co  tacaagcagcactgccctcccacacccgagaccagctgcgccacccagaccatcaccttc wt  tacaaacagcactgccctccaaccccggaaacttcctgtgcaacccagactatcacctttt co  gagagcttcaaggagaacctgaaggacttcctgctggtgatcccttcgactgctgggag wt  gaaagtttcaaagagaacctgaaggactttctgcttgtcatccccttttgactgtgggag co  cccgtgcaggagtga wt  ccagtccaggagtga
```

The invention claimed herein has been described generically, and by reference to specific embodiments. Examples and specific features are not intended to be limiting unless so indicated above. Modifications will occur to those of skill in the art, particularly in the selection of the source of mammalian GM-CSF, the specific codons optimized, the specific bases within the codons replaced to effect optimization, and the number and placement of the codons optimized, without departing from the invention, except as excluded by the claims set forth below.

---

What is claimed is:

1. An isolated nucleic acid which encodes human GM-CSF, said nucleic acid comprising Exons 1, 2, 3 and 4, wherein at least one of the Exons comprises at least one codon optimized for human expression;

wherein the Exons comprising Exon 1 are selected from the group consisting of SEQ ID NO: 2, SEQ ID NO: 3, SEQ ID NO: 4, and SEQ ID NO: 5;

wherein the Exons comprising Exon 2 are selected from the group consisting of SEQ ID NO: 7, SEQ ID NO: 8, and SEQ ID NO: 9;

wherein the Exons comprising Exon 3 are selected from the group consisting of SEQ ID NO: 11, SEQ ID NO: 12, SEQ ID NO: 13, and SEQ ID NO: 14;

and wherein the Exons comprising Exon 4 are selected from the following (1) and (2):

(1) in the case of sequence of native human Exon 4 encoding Ile at position 117, the Exons comprising Exon 4 are selected from the group consisting of SEQ ID NO: 16, SEQ ID NO: 17, SEQ ID NO: 18, SEQ ID NO: 19, SEQ ID NO: 20, and SEQ ID NO: 21;

and (2) in the case of sequence of native human Exon 4 encoding Thr at position 117, the Exons comprising Exon 4 are selected from the group consisting of SEQ ID NO: 22, SEQ ID NO:23, SEQ ID NO: 24, SEQ ID NO: 25, SEQ ID NO: 26, and SEQ ID NO: 27;

and wherein at least one of said Exons 1, 2, 3 and 4 is not human wild-type Exon.

2. The isolated nucleic acid of claim 1, wherein Exon 1 is SEQ ID NO: 2.

3. The isolated nucleic acid of claim 1, wherein Exon 1 is SEQ ID NO: 3.

4. The isolated nucleic acid of claim 1, wherein Exon 1 is SEQ ID NO: 4.

5. The isolated nucleic acid of claim 1, wherein Exon 1 is SEQ ID NO: 5.

6. The isolated nucleic acid of claim 1, wherein Exon 2 is SEQ ID NO: 7.

7. The isolated nucleic acid of claim 1, wherein Exon 2 is SEQ ID NO: 8.

8. The isolated nucleic acid of claim 1, wherein Exon 2 is SEQ ID NO: 9.

9. The isolated nucleic acid of claim 1, wherein Exon 3 is SEQ ID NO: 11.

10. The isolated nucleic acid of claim 1, wherein Exon 3 is SEQ ID NO: 12.

11. The isolated nucleic acid of claim 1, wherein Exon 3 is SEQ ID NO: 13.

12. The isolated nucleic acid of claim 1, wherein Exon 3 is SEQ ID NO: 14.

13. The isolated nucleic acid of claim 1, wherein the sequence of native human Exon 4 encodes Ile at position 117, and the Exons comprising Exon 4 are selected from the group consisting of SEQ ID NO: 16, SEQ ID NO: 17, SEQ ID NO: 18, SEQ ID NO: 19, SEQ ID NO: 20, and SEQ ID NO: 21.

14. The isolated nucleic acid of claim 1, wherein the sequence of native human Exon 4 encodes Thr at position 117, and the Exons comprising Exon 4 are selected from the group consisting of SEQ ID NO: 22, SEQ ID NO:23, SEQ ID NO: 24, SEQ ID NO: 25, SEQ ID NO: 26, and SEQ ID NO: 27.

15. A pharmaceutical composition comprising an effective amount of the isolated nucleic acid of claim 1, a vaccine, and a pharmaceutically acceptable carrier.

* * * * *

SEQUENCE LISTING

<160> NUMBER OF SEQ ID NOS: 34

<210> SEQ ID NO 1
<211> LENGTH: 147
<212> TYPE: DNA
<213> ORGANISM: Homo sapiens

<400> SEQUENCE: 1

```
atgtggctgc agagcctgct gctcttgggc actgtggcct gcagcatctc tgcacccgcc      60
cgctcgccca gccccagcac gcagccctgg gagcatgtga atgccatcca ggaggcccgg     120
cgtctcctga acctgagtag agacact                                         147
```

<210> SEQ ID NO 2
<211> LENGTH: 147
<212> TYPE: DNA
<213> ORGANISM: Homo sapiens

<400> SEQUENCE: 2

```
atgtggctgc agagcctgct cctgctgggc accgtggcct gcagcatcag cgctcccgcc      60
agaagcccca gccctccac ccagccctgg gagcacgtga acgccatcca ggaggccaga      120
cggctgctga acctgtccag agacacc                                         147
```

<210> SEQ ID NO 3
<211> LENGTH: 147
<212> TYPE: DNA
<213> ORGANISM: Homo sapiens

<400> SEQUENCE: 3

```
atgtggctgc agagcctgct gctcctgggc accgtggcct gcagcatcag cgcccccgcc      60
cgctcgccca gccccagcac gcagccctgg gagcacgtga acgccatcca ggaggcccgg     120
gcgctcctga acctgagccg cgacacc                                         147
```

<210> SEQ ID NO 4
<211> LENGTH: 147
<212> TYPE: DNA
<213> ORGANISM: Homo sapiens

<400> SEQUENCE: 4

```
atgtggctgc agagcctgct gctcctcggc actgtggcct gcagcatctc cgcacccgcc      60
cgctcgccca gccccagcac gcagccctgg gagcatgtga atgccatcca ggaggcccgg     120
cgtctcctga acctgtccag agacact                                         147
```

<210> SEQ ID NO 5
<211> LENGTH: 147
<212> TYPE: DNA
<213> ORGANISM: Homo sapiens

<400> SEQUENCE: 5

```
atgtggctgc agagcctgct gctcctcggc accgtggcct gcagcatctc cgcccccgcc      60
cgctcgccca gcccagcac gcagccctgg gagcacgtga acgccatcca ggaggcccgg     120
```

-continued

| gcgctcctga acctgtcccg cgacacc | 147 |

<210> SEQ ID NO 6
<211> LENGTH: 54
<212> TYPE: DNA
<213> ORGANISM: Homo sapiens

<400> SEQUENCE: 6

| gctgctgaga tgaatgaaac agtagaagtc atctcagaaa tgtttgacct ccag | 54 |

<210> SEQ ID NO 7
<211> LENGTH: 54
<212> TYPE: DNA
<213> ORGANISM: Homo sapiens

<400> SEQUENCE: 7

| gccgccgaga tgaacgagac cgtggaggtg atcagcgaga tgttcgacct gcag | 54 |

<210> SEQ ID NO 8
<211> LENGTH: 54
<212> TYPE: DNA
<213> ORGANISM: Homo sapiens

<400> SEQUENCE: 8

| gccgccgaga tgaacgaaac cgtggaggtc atcagcgaaa tgtttgacct ccag | 54 |

<210> SEQ ID NO 9
<211> LENGTH: 54
<212> TYPE: DNA
<213> ORGANISM: Homo sapiens

<400> SEQUENCE: 9

| gccgccgaga tgaatgagac cgtggaagtc atcagcgaga tgttcgacct ccag | 54 |

<210> SEQ ID NO 10
<211> LENGTH: 126
<212> TYPE: DNA
<213> ORGANISM: Homo sapiens

<400> SEQUENCE: 10

| gagccgacct gcctacagac ccgcctggag ctgtacaagc agggcctgcg gggcagcctc | 60 |
| accaagctca agggcccctt gaccatgatg gccagccact acaagcagca ctgccctcca | 120 |
| accccg | 126 |

<210> SEQ ID NO 11
<211> LENGTH: 126
<212> TYPE: DNA
<213> ORGANISM: Homo sapiens

<400> SEQUENCE: 11

| gagcccacct gtctgcagac ccggctggag ctgtacaagc agggactgcg ggcagcctg | 60 |
| accaagctga agggacccct gaccatgatg gccagccact acaagcagca ctgccctccc | 120 |
| acaccc | 126 |

<210> SEQ ID NO 12
<211> LENGTH: 126
<212> TYPE: DNA
<213> ORGANISM: Homo sapiens

<400> SEQUENCE: 12

| gagccgacct gcctgcagac ccgcctggag ctgtacaagc agggcctgcg cggcagcctc | 60 |

```
accaagctca agggcccct gaccatgatg gccagccact acaagcagca ctgccccccc    120
accccg                                                              126

<210> SEQ ID NO 13
<211> LENGTH: 126
<212> TYPE: DNA
<213> ORGANISM: Homo sapiens

<400> SEQUENCE: 13
gagccgacct gcctccagac ccgcctggag ctgtacaagc agggcctgcg cggcagcctc    60
accaagctca agggcccct caccatgatg gccagccact acaagcagca ctgccccccc    120
accccg                                                              126

<210> SEQ ID NO 14
<211> LENGTH: 126
<212> TYPE: DNA
<213> ORGANISM: Homo sapiens

<400> SEQUENCE: 14
gagccgacct gcctgcagac ccgcctggag ctgtacaagc agggcctgcg cggcagcctc    60
accaagctca agggcccct caccatgatg gccagccact acaagcagca ctgccccccc    120
accccg                                                              126

<210> SEQ ID NO 15
<211> LENGTH: 108
<212> TYPE: DNA
<213> ORGANISM: Homo sapiens

<400> SEQUENCE: 15
gaaacttcct gtgcaaccca gattatcacc tttgaaagtt tcaaagagaa cctgaaggac    60
tttctgcttg tcatcccctt tgactgctgg gagccagtcc aggagtga              108

<210> SEQ ID NO 16
<211> LENGTH: 108
<212> TYPE: DNA
<213> ORGANISM: Homo sapiens

<400> SEQUENCE: 16
gagaccagct gcgccaccca gatcatcacc ttcgagagct tcaaggagaa cctgaaggac    60
ttcctgctgg tgatcccctt cgactgctgg gagcccgtgc aggagtga              108

<210> SEQ ID NO 17
<211> LENGTH: 108
<212> TYPE: DNA
<213> ORGANISM: Homo sapiens

<400> SEQUENCE: 17
gagacctcct gcgccaccca gatcatcacc ttcgagagct tcaaggagaa cctgaaggac    60
ttcctgctgg tcatcccctt cgactgctgg gagcccgtcc aggagtga              108

<210> SEQ ID NO 18
<211> LENGTH: 108
<212> TYPE: DNA
<213> ORGANISM: Homo sapiens

<400> SEQUENCE: 18
gagacctcct gcgccaccca gatcatcacc ttcgagagct tcaaggagaa cctgaaggac    60
```

```
ttcctgctcg tcatcccctt cgactgctgg gagcccgtcc aggagtga          108
```

```
<210> SEQ ID NO 19
<211> LENGTH: 108
<212> TYPE: DNA
<213> ORGANISM: Homo sapiens

<400> SEQUENCE: 19
gagacctcct gcgccaccca gatcatcacc ttcgagtcct tcaaggagaa cctgaaggac   60
ttcctgctgg tcatcccctt cgactgctgg gagcccgtcc aggagtga              108
```

```
<210> SEQ ID NO 20
<211> LENGTH: 108
<212> TYPE: DNA
<213> ORGANISM: Homo sapiens

<400> SEQUENCE: 20
gaaacctcct gtgccaccca gatcatcacc ttcgaaagct tcaaggagaa cctgaaggac   60
ttcctgctgg tcatcccctt cgactgctgg gagcccgtcc aggagtga              108
```

```
<210> SEQ ID NO 21
<211> LENGTH: 108
<212> TYPE: DNA
<213> ORGANISM: Homo sapiens

<400> SEQUENCE: 21
gagacctcct gcgccaccca gatcatcacc ttcgagtcct tcaaggagaa cctgaaggac   60
ttcctgctcg tcatcccctt cgactgctgg gagcccgtcc aggagtga              108
```

```
<210> SEQ ID NO 22
<211> LENGTH: 108
<212> TYPE: DNA
<213> ORGANISM: Homo sapiens

<400> SEQUENCE: 22
gagaccagct gcgccaccca gaccatcacc ttcgagagct tcaaggagaa cctgaaggac   60
ttcctgctgg tgatcccctt cgactgctgg gagcccgtgc aggagtga              108
```

```
<210> SEQ ID NO 23
<211> LENGTH: 108
<212> TYPE: DNA
<213> ORGANISM: Homo sapiens

<400> SEQUENCE: 23
gagacctcct gcgccaccca gaccatcacc ttcgagagct tcaaggagaa cctgaaggac   60
ttcctgctgg tcatcccctt cgactgctgg gagcccgtcc aggagtga              108
```

```
<210> SEQ ID NO 24
<211> LENGTH: 108
<212> TYPE: DNA
<213> ORGANISM: Homo sapiens

<400> SEQUENCE: 24
gagacctcct gcgccaccca gaccatcacc ttcgagagct tcaaggagaa cctgaaggac   60
ttcctgctcg tcatcccctt cgactgctgg gagcccgtcc aggagtga              108
```

```
<210> SEQ ID NO 25
<211> LENGTH: 108
<212> TYPE: DNA
<213> ORGANISM: Homo sapiens
```

<400> SEQUENCE: 25
gagacctcct gcgccaccca gaccatcacc ttcgagtcct tcaaggagaa cctgaaggac     60
ttcctgctgg tcatcccctt cgactgctgg gagcccgtcc aggagtga     108

<210> SEQ ID NO 26
<211> LENGTH: 108
<212> TYPE: DNA
<213> ORGANISM: Homo sapiens

<400> SEQUENCE: 26
gaaacctcct gtgccaccca gatcatcacc ttcgaaagct tcaaggagaa cctgaaggac     60
ttcctgctgg tcatcccctt cgactgctgg gagcccgtcc aggagtga     108

<210> SEQ ID NO 27
<211> LENGTH: 108
<212> TYPE: DNA
<213> ORGANISM: Homo sapiens

<400> SEQUENCE: 27
gagacctcct gcgccaccca gaccatcacc ttcgagtcct tcaaggagaa cctgaaggac     60
ttcctgctcg tcatcccctt cgactgctgg gagcccgtcc aggagtga     108

<210> SEQ ID NO 28
<211> LENGTH: 108
<212> TYPE: DNA
<213> ORGANISM: Homo sapiens

<400> SEQUENCE: 28
gaaacttcct gtgcaaccca gactatcacc tttgaaagtt tcaaagagaa cctgaaggac     60
tttctgcttg tcatcccctt tgactgctgg gagccagtcc aggagtga     108

<210> SEQ ID NO 29
<211> LENGTH: 471
<212> TYPE: DNA
<213> ORGANISM: Mus musculus

<400> SEQUENCE: 29
atggctcacg agcggaaggc taaggtgctg cgcagaatgt ggctgcagaa cctgctgttc     60
ctgggcatcg tggtgtacag cctgagcgcc cccaccagaa gccccatcac cgtgaccaga     120
ccctggaagc acgtggaggc catcaaggaa gctctgaacc tgctggacga catgcccgtg     180
accctgaacg aggaggtgga ggtggtgagc aacgagttta gctttaagaa gctgacctgc     240
gtgcagaccc ggctgaagat cttcgagcag ggactgcggg caactttac caagctgaag     300 ggagccctga acatgaccgc cagctactac cagacctact gccctcccac acccgagacc     360
gactgtgaaa cccaggtgac cacctacgcc gactttatcg acagcctgaa gaccttcctg     420
accgacatcc ccttcgagtg taagaagccc gtgcagaagt gactcgagcg g     471

<210> SEQ ID NO 30
<211> LENGTH: 462
<212> TYPE: DNA
<213> ORGANISM: Mus musculus

<400> SEQUENCE: 30
atggcccacg agagaaaggc taaggtcctg aggaggatgt ggctgcagaa tttactttc     60 ctgggcattg tggtctacag cctctcagca cccacccgct cacccatcac tgtcacccgg     120

```
ccttggaagc atgtagaggc catcaaagaa gccctgaacc tcctggatga catgcctgtc    180
acattgaatg aagaggtaga agtcgtctct aacgagttct ccttcaagaa gctaacatgt    240
gtgcagaccc gcctgaagat attcgagcag ggtctacggg gcaatttcac caaactcaag    300
ggcgccttga acatgacagc cagctactac cagacatact gcccccaac tccggaaacg     360 gactgtgaaa cacaagttac cacctatgcg gatttcatag acagccttaa aacctttctg    420
actgatatcc cctttgaatg caaaaaacca gtccaaaaat ga                       462
```

<210> SEQ ID NO 31
<211> LENGTH: 435
<212> TYPE: DNA
<213> ORGANISM: Homo sapiens

<400> SEQUENCE: 31

```
atgtggctgc agagcctgct cctgctgggc accgtggcct gcagcatcag cgctcccgcc    60
agaagcccca gccctccac ccagccctgg gagcacgtga acgccatcca ggaggccaga     120
cggctgctga acctgtccag agacaccgcc gccgagatga cgagaccgt ggaggtgatc     180 agcgagatgt tcgacctgca ggagcccacc tgtctgcaga cccggctgga gctgtacaag    240
cagggactgc ggggcagcct gaccaagctg aagggacccc tgaccatgat ggccagccac    300
tacaagcagc actgccctcc cacacccgag accagctgcg ccacccagat catcaccttc    360
gagagcttca aggagaacct gaaggacttc ctgctggtga tccccttcga ctgctgggag    420
cccgtgcagg agtga                                                      435
```

<210> SEQ ID NO 32
<211> LENGTH: 435
<212> TYPE: DNA
<213> ORGANISM: Homo sapiens

<400> SEQUENCE: 32

```
atgtggctgc agagcctgct gctcttgggc actgtggcct gcagcatctc tgcacccgcc    60
cgctcgccca gccccagcac acagccctgg gagcatgtga atgccatcca ggaggcccgg    120
cgtctcctga acctgagtag agacactgct gctgagatga atgaaacagt agaagtcatc    180
tcagaaatgt ttgacctcca ggagccgacc tgcctacaga cccgcctgga gctgtacaag    240
cagggcctgc ggggcagcct caccaagctc aagggcccct tgaccatgat ggccagccac    300
tacaaacagc actgccctcc aaccccggaa acttcctgtg caacccagat tatcaccttt    360
gaaagtttca aagagaacct gaaggacttt ctgcttgtca tccccttcga ctgctgggag    420
ccagtccagg agtga                                                      435
```

<210> SEQ ID NO 33
<211> LENGTH: 435
<212> TYPE: DNA
<213> ORGANISM: Homo sapiens

<400> SEQUENCE: 33

```
atgtggctgc agagcctgct cctgctgggc accgtggcct gcagcatcag cgctcccgcc    60
agaagcccca gccctccac ccagccctgg gagcacgtga acgccatcca ggaggccaga     120
cggctgctga acctgtccag agacaccgcc gccgagatga cgagaccgt ggaggtgatc     180 agcgagatgt tcgacctgca ggagcccacc tgtctgcaga cccggctgga gctgtacaag    240
cagggactgc ggggcagcct gaccaagctg aagggacccc tgaccatgat ggccagccac    300
tacaagcagc actgccctcc cacacccgag accagctgcg ccacccagac catcaccttc    360
```

-continued

```
gagagcttca aggagaacct gaaggacttc ctgctggtga tccccttcga ctgctgggag    420
cccgtgcagg agtga                                                     435

<210> SEQ ID NO 34
<211> LENGTH: 435
<212> TYPE: DNA
<213> ORGANISM: Homo sapiens

<400> SEQUENCE: 34
atgtggctgc agagcctgct gctcttgggc actgtggcct gcagcatctc tgcacccgcc     60
cgctcgccca gccccagcac acagccctgg gagcatgtga atgccatcca ggaggcccgg    120
cgtctcctga acctgagtag agacactgct gctgagatga tgaaacagt agaagtcatc     180 tcagaaatgt ttgacctcca ggagccgacc tgcctacaga cccgcctgga gctgtacaag    240
cagggcctgc ggggcagcct caccaagctc aagggcccct tgaccatgat ggccagccac    300
tacaaacagc actgccctcc aaccccggaa acttcctgtg caacccagac tatcaccttt    360
gaaagtttca aagagaacct gaaggacttt ctgcttgtca tcccctttga ctgctgggag    420
ccagtccagg agtga                                                     435
```